(12) United States Patent
Winstead et al.

(10) Patent No.: US 6,206,192 B1
(45) Date of Patent: Mar. 27, 2001

(54) DENTAL EMERGENCY KIT

(75) Inventors: Herbert West Winstead, Walling; Rathnasabapathy Mohan, Sparta, both of TN (US)

(73) Assignee: Dendek Dental Products, Walling, TN (US)

( * ) Notice: Subject to any disclaimer, the term of this patent is extended or adjusted under 35 U.S.C. 154(b) by 0 days.

(21) Appl. No.: 09/420,144

(22) Filed: Oct. 18, 1999

(51) Int. Cl.[7] .................................................. A61C 19/02
(52) U.S. Cl. ........................ 206/572; 206/369; 206/63.5
(58) Field of Search .......................... 206/63.5, 83, 368, 206/369, 570–572

(56) References Cited

U.S. PATENT DOCUMENTS

| | | | |
|---|---|---|---|
| 4,294,349 | * 10/1981 | Isben et al. ........................ | 206/63.5 |
| 4,353,694 | * 10/1982 | Pelerin .............................. | 206/63.5 |
| 4,763,791 | * 8/1988 | Halverson et al. ................ | 206/570 |
| 4,828,113 | * 5/1989 | Friedland et al. ................. | 206/570 |
| 5,289,919 | * 3/1994 | Fischer ............................. | 206/571 |
| 5,501,602 | 3/1996 | Anderson et al. . | |
| 5,507,643 | 4/1996 | Klein . | |
| 5,634,792 | 6/1997 | Brisendine . | |
| 5,660,546 | 8/1997 | Shafer . | |
| 6,050,815 | * 4/2000 | Adam et al. ...................... | 433/9 |

OTHER PUBLICATIONS

Dental First Aid Kit—2 pages.

* cited by examiner

*Primary Examiner*—Jim Foster
(74) *Attorney, Agent, or Firm*—Luedeka, Neely & Graham PC

(57) ABSTRACT

A kit for the emergency treatment of dental conditions. The kit includes a container and a plurality of dental treatment components positioned within the container, the dental treatment components being selected from the group consisting of dental cement or components thereof, an anesthetic, an antiseptic, sorbent material for wrapping around teeth to be treated or for packing into apertures of the teeth to be treated such as resulting from broken teeth, missing teeth, missing or broken fillings, or crowns or bridges, and tools for manipulating the dental cement and the sorbent material.

9 Claims, 1 Drawing Sheet

DENTAL EMERGENCY KIT

FIELD OF INVENTION

The invention relates to a kit for providing emergency dental aid. More particularly, the invention relates to a portable and compact kit which provides emergency aid for the temporary relief of dental problems such as dry sockets, loose crowns, damaged bridges, lost or broken fillings, broken teeth and avulsed teeth.

BACKGROUND OF THE INVENTION

In certain circumstances, it is desirable to enable quick treatment of dental emergencies. For example, should a dental injury occur remote from a dental facility, such as when camping, a quick response can alleviate pain and discomfort and avoid or reduce the further injury or damage.

Accordingly, it is an object of the present invention to provide a dental emergency kit which allows non-dentists to provide temporary aid in the event of dental crises.

Another object of the invention is to provide a kit of the character described having a collection of materials suitable for enabling temporary alleviation of pain associated with dental emergencies.

A further object of the invention is to provide a kit of the character described having a sufficiently wide variety of materials to enable treatment of numerous types of dental problems.

Yet an additional object of the invention is to provide a kit of the character described that is economical and convenient to use.

A still further object of the invention is to provide a kit of the character described that is compact and convenient to transport.

Yet a further object of the invention is to provide a dental emergency kit having a relatively long shelf life.

SUMMARY OF THE INVENTION

With regard to the foregoing and other objects, the invention provides a kit for the emergency treatment of dental conditions.

In a preferred embodiment, the kit includes a container and a plurality of dental treatment components positioned within the container. The dental treatment components include dental cement or components thereof, an anesthetic, an antiseptic, sorbent material for wrapping around teeth to be treated or for packing into apertures of the teeth to be treated such as resulting from broken teeth, missing teeth, missing or broken fillings, or crowns or bridges, and tools for manipulating the dental cement and the sorbent material.

Also disclosed are methods for treating various dental conditions, such as dry sockets, loose crowns, damaged bridges, lost or broken fillings, broken teeth and avulsed teeth, using the components of the kit.

The kit and methods of the invention advantageously enable the temporary treatment of various dental conditions when access to a dentist is not available. Prompt treatment of the dental conditions can alleviate pain and discomfort to the patient and, in many instances, the prompt treatment can serve to reduce additional injury.

BRIEF DESCRIPTION OF THE DRAWING

Further advantages of the invention will become apparent by reference to the detailed description of the preferred embodiments, when considered in conjunction with the figure, which is not to scale, and wherein.

DETAILED DESCRIPTION OF THE DRAWINGS

Figure 1:
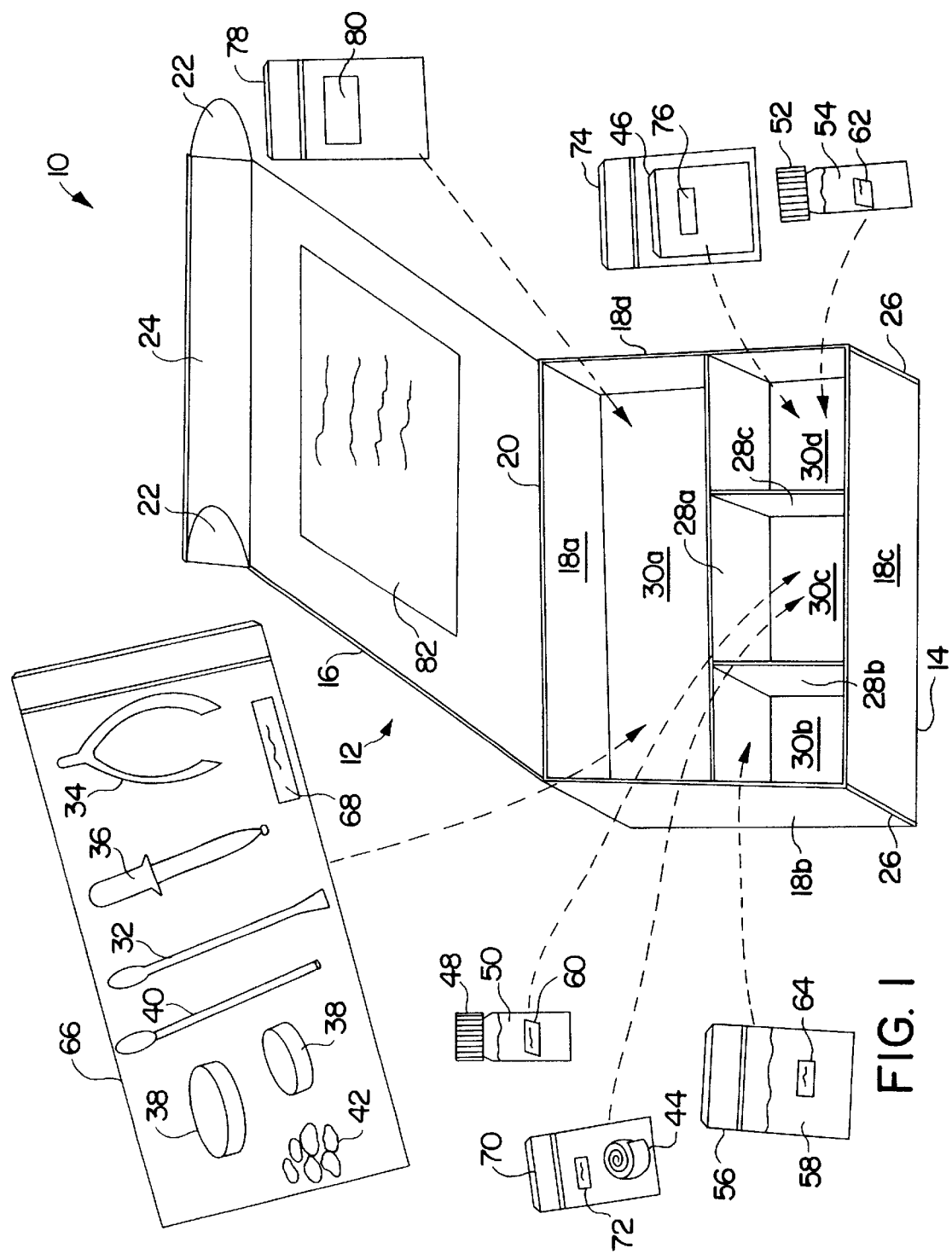
FIG. 1 is a front partial elevation view of a dental emergency kit in accordance with a preferred embodiment of the invention..

Referring now to FIG. 1, the components of a preferred dental emergency kit 10 in accordance with the invention are shown. The kit 10 is intended to enable the administration of temporary relief to a person who has experienced dental crises including dry sockets, loose crowns, broken bridges, lost fillings, broken teeth, and knocked-out or avulsed teeth.

The kit 10 is preferably compact and lightweight so as to be suitable for transporting to remote areas such as when camping, or for storage in a suitcase, automobile or the like. In a preferred embodiment, the kit 10 includes a lightweight and compact container, such as a paperboard box 12 having a bottom portion 14 and a lid 16 hingedly attached to an uppermost portion of a sidewall 18a of the bottom portion 14 along fold line 20. A pair of flaps 22 preferably extend from a panel 24 attached to the lid 16 for being received within apertures 26 defined on the bottom portion 14 for maintaining the lid in a closed position.

In addition to the sidewall 18a, the bottom portion 14 also includes sidewalls 18b, 18c and 18d. A plurality of interior sidewalls are preferably located within the bottom portion 14 for defining a plurality of discrete compartments for storage of dental components of the kit 10. For example, in a preferred embodiment, the bottom portion 14 includes sidewall 28a extending between the sidewalls 18b and 18d, and sidewalls 28b and 28c extending between the sidewall 28a and the sidewall 18c. Collectively, the sidewalls of the bottom portion 14 define discrete compartments 30a, 30b, 30c and 30d. Other suitable materials for providing the container include metal, such as aluminum, plastics and other polymeric materials. For containers made of plastic and the like, a waterproof seal may be provided at the junction of the lid and the bottom portion.

The assembled kit 10 preferably includes sufficient dental components to enable treatment of a variety of dental conditions involving dry socket, crowns and bridges, lost or broken fillings, knocked out teeth and broken teeth. To enable treatment of the foregoing dental conditions, the kit 10 preferably includes a plurality of hand tools and packing/sorbent components. Examples of preferred tool components include spatula 32, dental tweezers 34, medicine dropper 36, mixing bowls 38 and cotton swabs 40. Preferred packing/sorbent components include cotton pellets 42, iodoform gauze 44 and plain gauze 46. It will be understood that the cotton swabs 40 are also sorbent and can be used to dry teeth and the like as well as to manipulate the cement and position gauze.

In addition, the kit 10 also preferably includes mixable liquid components and powder components that are pliable immediately after mixing but set into a relatively hard compound suitable for serving as a dental cement and to provide temporary filings. Other desired components include components having antiseptic and anesthetic properties. The foregoing objectives of having suitable liquid and powder components and antiseptic and anesthetic components is preferably achieved in a compact manner as by including in the kit 10 a reclosable vial 48 of eugenol 50, a reclosable vial 52 of saline solution 54 and a reclosable plastic bag 56 containing zinc oxide powder 58. The term "reclosable" refers to the ability to access and re-access the bag, with suitable recloseability being provided by conventional plastic bags having mating plastic seals or so-called "zip locks."

The eugenol 50 is a colorless aromatic liquid phenol ($C_{10}H_{12}O_2$) typically derived from clove oil. The vial 48 is preferably a brown glass or plastic vial having a reclosable cap. The eugenol has both antiseptic and anesthetic properties.

The saline solution has antiseptic properties. The vial 52 is similar in size and construction to the vial 48, but is preferably clear so as to readily distinguish between the vials. To further aid in identification, the vial 48 preferably includes a label 60 bearing indicia such as "Eugenol," and the vial 52 preferably includes a label 62 bearing indicia such as "Saline Solution."

The zinc oxide powder 58 serves as a binder and is mixable with the eugenol. The mixture is pasty or pliable after mixing but sets within a few minutes into a relatively hard compound suitable for use as a dental cement and temporary filling material. The bag 56 preferably contains zinc oxide powder and includes a label 64 bearing indicia such as "Zinc Oxide Powder".

To facilitate use of the kit 10 by a person not having training in dental procedures and equipment, the components (except for the vials 48 and 52) are preferably packaged in reclosable bags (such as the bag 56) having labels bearing indicia corresponding to the contents. Each bag is preferably stored in one of the compartments 30a–30d. For example, spatula 32, dental tweezers 34, medicine dropper 36, mixing bowls 38, cotton swabs 40 and cotton pellets 42 are preferably packaged in reclosable bag 66 having a label 68 bearing indicia corresponding to these contents. The bag 66 is preferably stored in compartment 30a.

The bag 56 of zinc oxide powder 58 is stored in compartment 30b. The vial 48 of eugenol 50 and a bag 70 containing the iodoform gauze 44 with suitable label 72 are stored in compartment 30c. The vial 52 of saline solution 54 and a bag 74 containing the gauze 46 with suitable label 76 is stored in compartment 30d. An empty reclosable fluid impervious container such as a plastic bag 78 bearing a label 80 with the indicia "Broken Tooth Bag" or the like is preferably provided for storing broken teeth for transporting the tooth to the dentist. The bag 78 is preferably stored in the compartment 30a.

A sheet 82 bearing information about the kit and instructions detailing use of the kit 10 for various dental conditions is preferably provided with the kit and removably insertable into a pocket on the lid or secured, as by adhesive, to an inner surface of the lid 16 for quick and convenient reference by the user of the kit 10. The instructions may likewise be printed on the container or otherwise made suitable accessible to the user. Preferred information for inclusion on the sheet 82 is as follows:

| | |
|---|---|
| Basic Mix: | READ INSTRUCTIONS CAREFULLY BEFORE USE |
| Place ⅛ tsp of zinc oxide powder in the mixing bowl. With medicine dropper add one drop of eugenol. With a spatula stir and slowly add more zinc oxide powder or eugenol until paste is the consistency of oatmeal. | Place a towel under the mixing bowl as eugenol will stain many materials including Formica. |
| | FOR DRY SOCKET: Rinse mouth thoroughly with hydrogen peroxide or warm salt water, carefully rinsing the food particles out of the socket where tooth was extracted. Cut a small strip of iodoform gauze and saturate in eugenol. Use dental tweezers and place the iodoform gauze in the socket. See your dentist as soon as possible |
| | FOR CROWNS & BRIDGES: Clean the inside of the crown/s in plain water and dry thoroughly with cotton swab. Use basic mix and apply to inside of the crown/s. Place crown or bridge on tooth and bite gently on plain gauze for 3 to 5 minutes until crown or bridge is secure. See your dentist as soon as possible. |
| Contents: Zinc oxide powder, eugenol liquid, iodoform gauze, plain gauze, normal saline solution, cotton pellets, spatula, dental tweezers, plastic bag, medicine dropper and mixing bowls | FOR LOST OR BROKEN FILLING: Dry tooth with clean cloth. With dental tweezers, dip a cotton pellet in the basic mix and place it in the tooth where the filling was lost. Pat evenly with wet cotton pellet or cotton swab until the bite is comfortable. See your dentist as soon as possible. |
| | FOR KNOCKED OUT TOOTH: Wrap tooth in plain gauze. Place tooth and gauze in reclosable plastic bag marked "For Knocked Out Tooth." Pour enough saline solution over the gauze in the bag to thoroughly saturate the gauze. See your dentist as soon as possible. |
| | FOR BROKEN TOOTH: Soak cotton pellet in eugenol and gently swab broken area. Then apply basic mix to the broken edge. See your dentist as soon as possible. |
| | KEEP OUT OF REACH OF CHILDREN |

The invention advantageously provides a compact and highly transportable kit for the treatment of various dental conditions by persons having no training in dental procedures. The instructions provide methods for using the materials of the kit to treat dental conditions. The kit and its instructions enable emergency treatment of such dental conditions which may reduce discomfort to the patient and avoid or reduce additional injury.

The foregoing description of certain embodiments of the present invention has been provided for purposes of illustration only, and it is understood that numerous modifications, alterations or additions thereto may be made in and to the illustrated embodiments without departing from the spirit and scope of the invention as defined in the following claims.

What is claimed is:

1. A kit for providing emergency dental aid such as temporary relief of dental crises relating to dry sockets, loose crowns, damaged bridges, lost or broken fillings, broken teeth and avulsed teeth, said kit comprising:

a) an encapsulated quantity of powdered zinc oxide;
   b) an encapsulated quantity of liquid eugenol;
   c) an encapsulated quantity of saline solution;
   d) a quantity of iodoform gauze for use in packing dry sockets;

e) a quantity of plain gauze for repair of crowns and bridges and for temporary storage of avulsed teeth;

f) a plurality of cotton pellets for temporary repair of lost or broken fillings and for repair of broken teeth;

g) a spatula for mixing the eugenol and zinc oxide;

h) tweezers for placing iodoform gauze in dry sockets, for manipulating cotton pellets and for use in repairing lost or broken fillings and broken teeth;

i) a plurality of cotton swabs for repair of crowns, bridges and lost or broken fillings;

j) a medicine dropper for measuring and adding eugenol to zinc oxide powder for preparing a temporary dental cement;

k) a plurality of mixing bowls for containing and mixing eugenol and zinc oxide powder for preparing a temporary dental cement;

l) a reclosable container dimensioned for temporarily preserving avulsed teeth;

m) instructions for providing emergency dental aid; and, n) a package for containing the foregoing components a-m.

2. The kit of claim 1, further comprising indicia on the encapsulated containers of powdered zinc oxide, liquid eugenol, saline solution, iodoform gauze and plain gauze to indicate the contents of the encapsulated containers.

3. The kit of claim 1 wherein the encapsulated containers of powdered zinc oxide, iodoform gauze and plain gauze are resealable plastic bags.

4. The kit of claim 1 wherein the encapsulated containers of liquid eugenol and saline solution are resealable vials.

5. The kit of claim 1 wherein the cotton pellets, spatula, tweezers, cotton swabs, medicine dropper and mixing bowls are contained together in a encapsulated container.

6. The kit of claim 5 wherein the encapsulated container for containing the cotton pellets, spatula, tweezers, cotton swabs, medicine dropper and mixing bowls is a reclosable bag.

7. The kit of claim 1 wherein the instructions are printed on a sheet secured to the package for containing the kit components.

8. The kit of claim 1 wherein the package for containing the kit components is a paperboard container having a plurality of discrete compartments.

9. A kit for the emergency treatment of dental conditions, the kit comprising a container and a plurality of dental treatment components positioned within the container, the dental treatment components being selected from the group consisting of dental cement or components thereof, an anesthetic, an antiseptic, sorbent material for wrapping around teeth to be treated or for packing into apertures of the teeth to be treated such as resulting from broken teeth, missing teeth, missing or broken fillings, or crowns or bridges, and tools for manipulating the dental cement and the sorbent material, the tools being selected from the group consisting of tweezers, spatulas and cotton swabs.

* * * * *